(12) United States Patent
Jervis

(10) Patent No.: US 6,562,056 B2
(45) Date of Patent: *May 13, 2003

(54) BALLOON DEVICE FOR USE IN SURGERY AND METHOD OF USE

(75) Inventor: James E. Jervis, San Mateo, CA (US)

(73) Assignee: General Surgical Innovations, Inc., Norwalk, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/945,604

(22) Filed: Sep. 4, 2001

(65) Prior Publication Data

US 2002/0032456 A1 Mar. 14, 2002

Related U.S. Application Data

(60) Continuation of application No. 08/924,350, filed on Sep. 5, 1997, which is a continuation of application No. 08/570,766, filed on Dec. 12, 1995, now Pat. No. 5,772,680, which is a continuation-in-part of application No. 08/403,012, filed on Mar. 10, 1995, now Pat. No. 5,540,711, which is a continuation-in-part of application No. 08/388,233, filed on Feb. 13, 1995, now Pat. No. 5,730,756, which is a continuation-in-part of application No. 08/267,488, filed on Jun. 29, 1994, now Pat. No. 5,607,443, which is a continuation-in-part of application No. 08/124,283, filed on Sep. 20, 1993, now Pat. No. 5,836,961, which is a continuation-in-part of application No. 08/073,737, filed on Jun. 8, 1993, now abandoned, which is a division of application No. 07/893,988, filed on Jun. 2, 1992, now Pat. No. 6,312,442.

(51) Int. Cl.$^7$ .............................................. A61B 17/00

(52) U.S. Cl. ..................... 606/190; 600/207; 604/96.01

(58) Field of Search ................................. 600/201, 204, 600/207, 210; 604/96.01–109; 606/190–200, (56) References Cited

U.S. PATENT DOCUMENTS

| | | |
|---|---|---|
| 512,456 A | 9/1894 | Sadilkova |
| 1,213,005 A | 1/1917 | Pillsbury |
| 2,936,760 A | 5/1960 | Gants |
| 3,545,443 A | 12/1970 | Ansari et al. |
| 3,774,596 A | 11/1973 | Cook |
| 3,800,788 A | 4/1974 | White |
| 3,882,852 A | 5/1975 | Sinnreich |
| RE29,207 E | 5/1977 | Boldac et al. |
| 4,217,889 A | 8/1980 | Radovan |
| 4,243,050 A | 1/1981 | Littleford |
| 4,276,874 A | 7/1981 | Wolvek et al. |
| 4,312,353 A | 1/1982 | Shahbabian |
| 4,411,654 A | 10/1983 | Boarini et al. ............. 604/165 |
| 4,490,137 A | 12/1984 | Moukheibir ................ 604/28 |
| 4,496,345 A | 1/1985 | Hasson ...................... 604/103 |
| 4,574,806 A | 3/1986 | McCarthy |
| 4,581,025 A | 4/1986 | Timmermans ............. 604/264 |
| 4,596,554 A | 6/1986 | Dastgeer .................... 604/54 |
| 4,644,936 A | 2/1987 | Schiff |
| 4,654,030 A | 3/1987 | Moll et al. .................. 604/165 |
| 4,685,447 A | 8/1987 | Iverson et al. |
| 4,738,666 A | 4/1988 | Fuqua ........................ 604/104 |

(List continued on next page.)

FOREIGN PATENT DOCUMENTS

| | | | |
|---|---|---|---|
| SU | 797668 | 1/1981 | ................ 600/207 |
| WO | WO 92/06638 | 4/1992 | |
| WO | WO 93/09772 | 5/1993 | |
| WO | WO 95/32663 | 12/1995 | |

Primary Examiner—Glenn K. Dawson (57) ABSTRACT

A balloon device useful for dissecting tissue or retracting tissue for the purpose of providing space for laproscopic surgery includes a balloon having at least two protuberances in its distal region. The present device is particularly useful in bladder neck suspension and hernia repair procedures.

4 Claims, 7 Drawing Sheets

U.S. PATENT DOCUMENTS

| | | | | |
|---|---|---|---|---|
| 4,769,038 A | | 9/1988 | Bendavid et al. | 623/13 |
| 4,772,266 A | | 9/1988 | Groshong | 604/164 |
| 4,779,611 A | | 10/1988 | Grooters et al. | |
| 4,784,133 A | | 11/1988 | Mackin | |
| 4,793,348 A | | 12/1988 | Palmaz | |
| 4,798,205 A | | 1/1989 | Bonomo et al. | |
| 4,800,901 A | | 1/1989 | Rosenberg | |
| 4,802,479 A | | 2/1989 | Haber et al. | |
| 4,813,429 A | | 3/1989 | Eshel et al. | |
| 4,854,316 A | | 8/1989 | Davis | |
| 4,869,717 A | | 9/1989 | Adair | |
| 4,888,000 A | | 12/1989 | McQuilkin et al. | |
| 4,917,668 A | | 4/1990 | Haindi | |
| 4,931,042 A | | 6/1990 | Holmes et al. | |
| 4,955,895 A | | 9/1990 | Sugiyama et al. | 606/194 |
| 4,994,071 A | | 2/1991 | MacGregor | 606/194 |
| 5,002,557 A | | 3/1991 | Hasson | 606/101 |
| 5,009,643 A | | 4/1991 | Reich et al. | 604/165 |
| 5,015,231 A | | 5/1991 | Keith et al. | 604/96 |
| 5,030,206 A | | 7/1991 | Lander | 604/164 |
| 5,030,227 A | | 7/1991 | Rosenbluth et al. | 604/192 |
| 5,074,871 A | | 12/1991 | Groshong | 606/170 |
| 5,104,383 A | | 4/1992 | Shichman | 604/167 |
| 5,116,305 A | * | 5/1992 | Milder et al. | 600/18 |
| 5,116,318 A | | 5/1992 | Hillstead | 604/96 |
| 5,116,357 A | | 5/1992 | Eberbach | 606/213 |
| 5,122,155 A | | 6/1992 | Eberbach | 606/213 |
| 5,137,512 A | | 8/1992 | Burns et al. | 604/96 |
| 5,141,494 A | | 8/1992 | Danforth et al. | 604/96 |
| 5,141,515 A | | 8/1992 | Eberbach | 606/151 |
| 5,147,302 A | | 9/1992 | Euteneuer et al. | 604/103 |
| 5,147,374 A | | 9/1992 | Fernandez | 606/151 |
| 5,158,545 A | | 10/1992 | Trudell et al. | 604/53 |
| 5,159,925 A | | 11/1992 | Neuwirth et al. | |
| 5,163,949 A | | 11/1992 | Bonutti | 606/192 |
| 5,176,692 A | | 1/1993 | Wilk et al. | 606/151 |
| 5,183,463 A | | 2/1993 | Debbas | 604/98 |
| 5,188,596 A | | 2/1993 | Condon et al. | 604/101 |
| 5,188,630 A | | 2/1993 | Christoudias | 606/1 |
| 5,195,507 A | | 3/1993 | Bilweis | |
| 5,201,754 A | | 4/1993 | Crittenden et al. | 606/194 |
| 5,209,725 A | | 5/1993 | Roth | 604/53 |
| 5,215,526 A | | 6/1993 | Deniega et al. | 604/164 |
| 5,222,970 A | | 6/1993 | Reeves | 606/195 |
| 5,226,890 A | | 7/1993 | Ianniruberto et al. | 604/164 |
| 5,232,446 A | | 8/1993 | Arney | 604/96 |
| 5,258,026 A | | 11/1993 | Johnson et al. | 623/8 |
| 5,269,753 A | | 12/1993 | Wilk | 604/49 |
| 5,308,327 A | | 5/1994 | Heaven et al. | 604/96 |
| 5,309,896 A | | 5/1994 | Moll et al. | |
| 5,314,443 A | | 5/1994 | Rudnik | 604/192 |
| 5,318,012 A | | 6/1994 | Wilk | |
| 5,342,307 A | | 8/1994 | Euteneuer et al. | 604/103 |
| 5,346,504 A | | 9/1994 | Ortiz et al. | 606/192 |
| 5,359,995 A | | 11/1994 | Sewell, Jr. | |
| 5,361,752 A | | 11/1994 | Moll et al. | |
| 5,370,134 A | | 12/1994 | Chin et al. | |
| 5,383,889 A | | 1/1995 | Warner et al. | |
| 5,402,772 A | | 4/1995 | Moll et al. | |
| 5,407,433 A | | 4/1995 | Loomas | 604/167 |
| 5,431,173 A | | 7/1995 | Chin et al. | |
| 5,439,476 A | | 8/1995 | Frantzides | 606/192 |
| 5,468,248 A | | 11/1995 | Chin et al. | 600/207 |
| 5,490,839 A | | 2/1996 | Wang et al. | 604/96 |
| 5,505,698 A | | 4/1996 | Booth et al. | 604/96 |
| 5,527,264 A | | 6/1996 | Moll et al. | 600/204 |
| 5,540,711 A | | 7/1996 | Kieturakis et al. | 600/207 |
| 5,588,951 A | | 12/1996 | Zhu et al. | 600/207 |
| 5,653,690 A | | 8/1997 | Booth et al. | 604/96 |
| 5,690,668 A | | 11/1997 | Fogarty et al. | 606/192 |
| 5,720,762 A | | 2/1998 | Bass | 606/192 |
| 5,730,748 A | | 3/1998 | Fogarty et al. | 600/207 |
| 5,772,680 A | * | 6/1998 | Kieturakis et al. | 606/190 |
| 6,013,090 A | | 1/2000 | Fogarty et al. | 606/190 |

* cited by examiner

BALLOON DEVICE FOR USE IN SURGERY AND METHOD OF USE

RELATED APPLICATIONS

This application is a Continuation of prior application Ser. No. 08/924,350 filed Sep. 5, 1997 now pending, which is a Continuation of Ser. No. 08/570,776 filed on Dec. 12, 1995 now U.S. Pat. No. 5,772,680, which is a Continuation-In-Part of Ser. No. 08/403,012 filed on Mar. 10, 1995, now U.S. Pat. No. 5,540,711, which is a Continuation-In-Part of Ser. No. 08/388,233 filed on Feb. 13, 1995, now U.S. Pat. No. 5,730,756, which is a Continuation-In-Part of Ser. No. 08/267,488 filed on Jun. 29, 1994, now U.S. Pat. No. 5,607,443, which is a Continuation-In-Part of Ser. No. 08/124,283 filed on Sep. 20, 1993, now U.S. Pat. No. 5,836,961, which is a Continuation-In-Part of Ser. No. 08/073,737 filed on Jun. 8, 1993, now abandoned, which is a Divisional of Ser. No. 07/893,988 filed on Jun. 2, 1992, now U.S. Pat. No. 6,312,442.

FIELD OF THE INVENTION

The present invention constitutes specially shaped balloon dissection or retraction devices and their use. The invention relates generally to an apparatus and method for developing an anatomic space for laproscopic procedures and, more specifically, to an apparatus and method particularly suitable for surgical procedures in which there is a need to dissect around an obstruction or around an area which it would be undesirable to dissect. The present invention provides a device which can be used to dissect around a hernia and in bladder neck suspension procedures, also known as urethropoxy, in which avoidance of the pubic symphysis is desirable.

SUMMARY OF THE INVENTION

The present invention comprises a balloon suitable for tissue dissection or tissue retraction which has at least two protuberances (which may be referred to as "legs", "arms", "horns" or other descriptive term) at its distal region and its method of use.

These protuberances may be relatively large relative to the remainder of the balloon or they may be relatively small, depending upon the anatomy of the region in which the balloon is to be used. The purpose of the protuberances is to achieve dissection in the desired location and to avoid dissection where it would be detrimental to the patient.

DETAILED DESCRIPTION OF THE INVENTION

Figure 2:
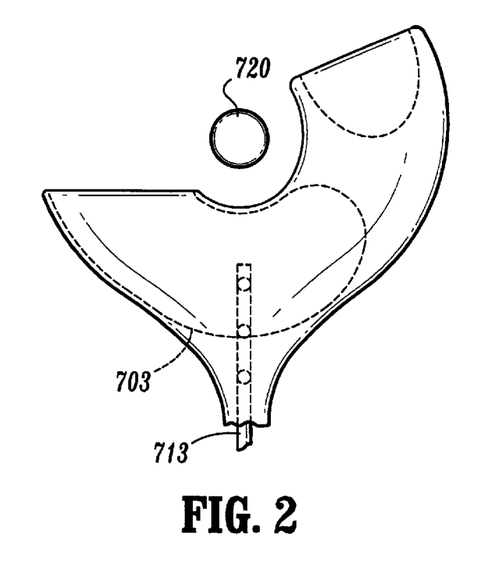
FIG. 2 shows the balloon of FIG. 1 in a partially inflated state.
Figure 3:
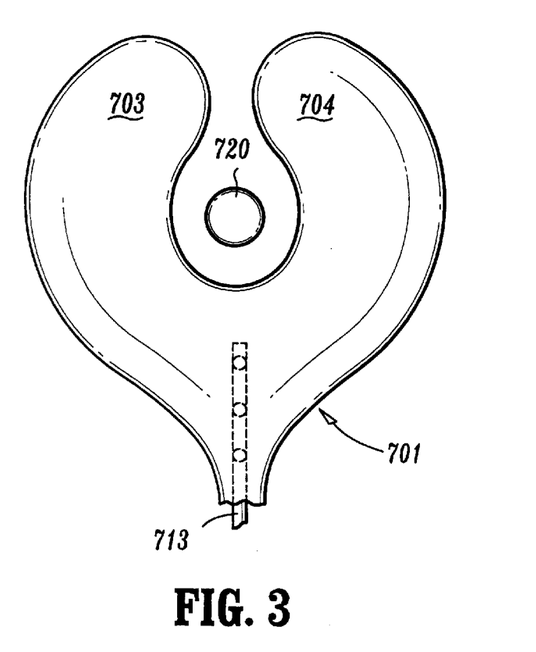
FIG. 3 shows the balloon of FIG. 1 in a fully inflated state.

The balloon devices described and claimed herein are suitable for the various uses disclosed in the parent and other applications identified herein which have been incorporated herein by reference. In connection with the present invention it has been found that in certain surgical procedures there is a need to dissect around an obstruction as for example a hernia. For this purpose, a horseshoe-shaped or bifurcated balloon 701, which is preferably nonelastic, e.g., made from polyurethane or polyvinyl chloride, is provided as shown in FIGS. 1–4. The balloon 701 is substantially Y-shaped as shown in FIG. 3 and is provided with a bifurcation which leads into legs 703 and 704 to provide a U-shaped space therebetween. The balloon 701 can be constructed in the manner hereinbefore described for the previous balloons used in accordance with the present invention.

Figures 1, 4:
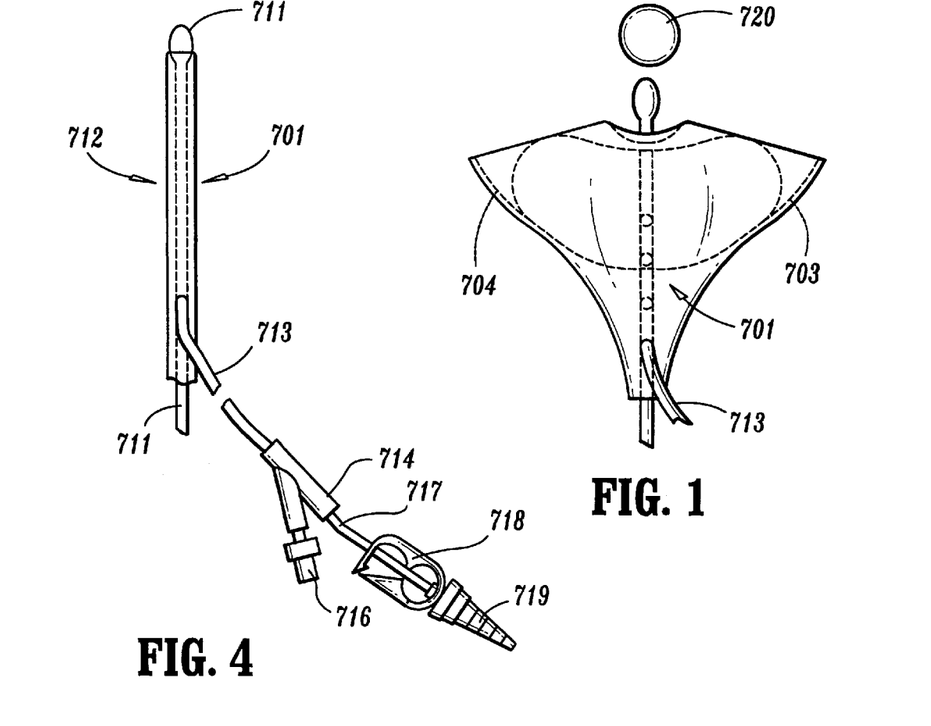
FIG. 1 is a diagrammatic view of an embodiment of this invention in which the protuberances are relatively large and are folded back into the interior of the balloon in its deflated state.
FIG. 4 shows the balloon of FIG. 1 rolled on a guide rod.

The legs 703 and 704 can be folded back or inverted into the bifurcation as shown in FIG. 1 and then can be rolled into two rolls, rolled in from opposite sides onto an olive-tipped guide rod 711 shown in FIG. 4 and held in place by a separate balloon cover (not shown) or by the use of flaps forming a sleeve (not shown) to provide an assembly 712. It has been found that in connection with the present invention to achieve the best dissection capabilities for the balloon and expansion of the balloon, the balloon 701 is secured to the guide rod or tunneling rod 711 so that the guide rod underlies the balloon. The side margins are rolled inwardly into two rolls so that the two rolls face downwardly toward the tunneling guide rod 711. They are then brought into close proximity with each other to form a single roll and secured to the tunneling guide rod 711 as hereinbefore described. A tubular member 713 providing a balloon inflation lumen opening into the interior of the balloon 701 is sealed into the balloon 701. A Y adapter 714 is secured to the tubular member 713 and carries a male fitting 716 and another tubular member 717 on which there is mounted a tubing clamp 718 and another male fitting 719.

Let it be assumed that it is desired to dissect around an obstruction 720 which by way of example can be ventral hernia or other obstruction that cannot be readily dissected. Let it also be assumed that the assembly 712 shown in FIG. 4 as been introduced into a space with or without a laproscope and an obstruction 720 is encountered and it is desired to dissect around the obstruction 720. This can be accomplished by removing the cover or sleeve (not shown) that was used for enclosing the balloon 701 and securing it to the guide rod 711. As soon as the balloon 701 is released, it can be inflated through the tubular member 713 to unroll sideways or laterally in a plane just proximal of the obstruction 720. The balloon 701, because of the manner in which it was rolled up, will unroll downwardly and outwardly away from the tunneling guide rod 711 to create the desired dissection. Continued inflation of the balloon will cause one or both the legs 703 and 704 to progressively evert and advance around the obstruction 720. Thus, as shown in FIG. 2, the arm 704 everts and passes around one side of the obstruction 720 while accomplishing dissection as it goes, whereas the other arm 703 can thereafter or simultaneously evert to cause dissection around the other side of the obstruction 720 until both of the legs 703 and 704 are completely inflated to create a dissection extending around the obstruction 720. The balloon 701 can then be deflated and removed. The dissected space can then be insufflated and surgical procedures can thereafter be performed in the insufflated space. Alternatively, a mechanical retractor, which may be, e.g., a toroidal balloon, may be used to maintain the dissected space in an "open" condition to facilitate the surgical procedures.

Figure 5:
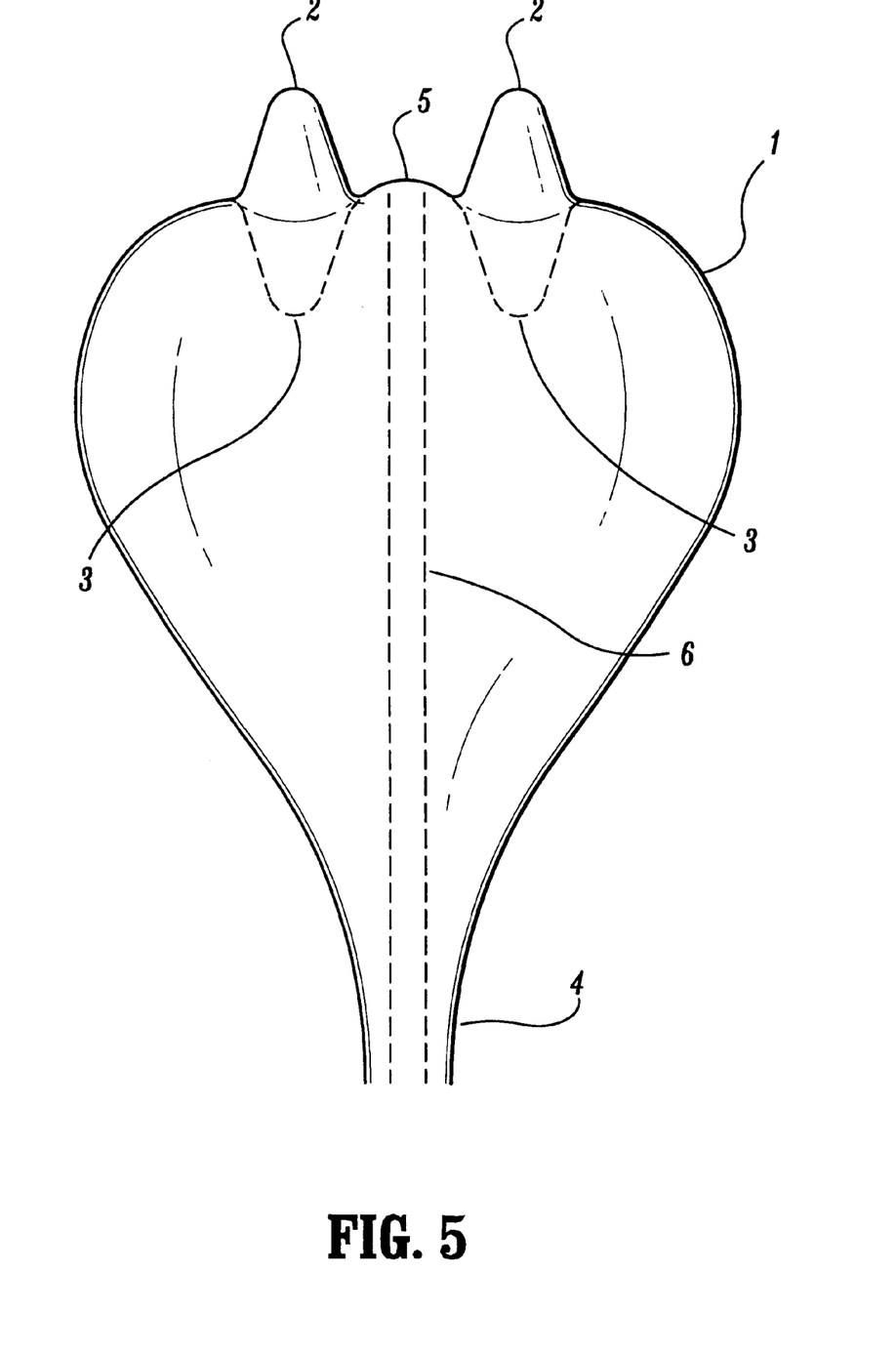
FIG. 5 is a plan view of a balloon having an alternate shape contemplated by the present invention.
Figure 6:
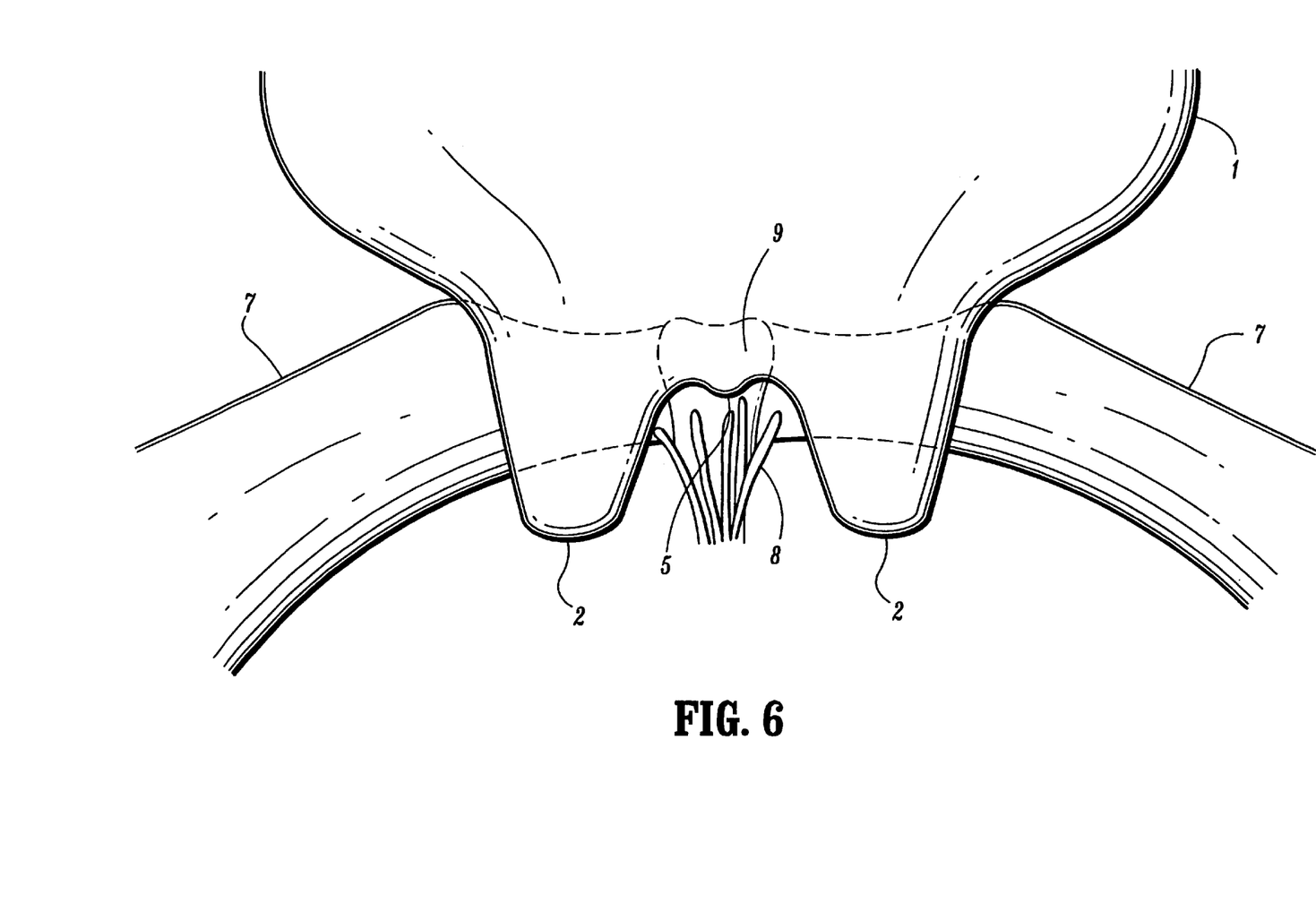
FIG. 6 shows the balloon of FIG. 5 after it has been inflated to dissect tissue.
Figure 7:
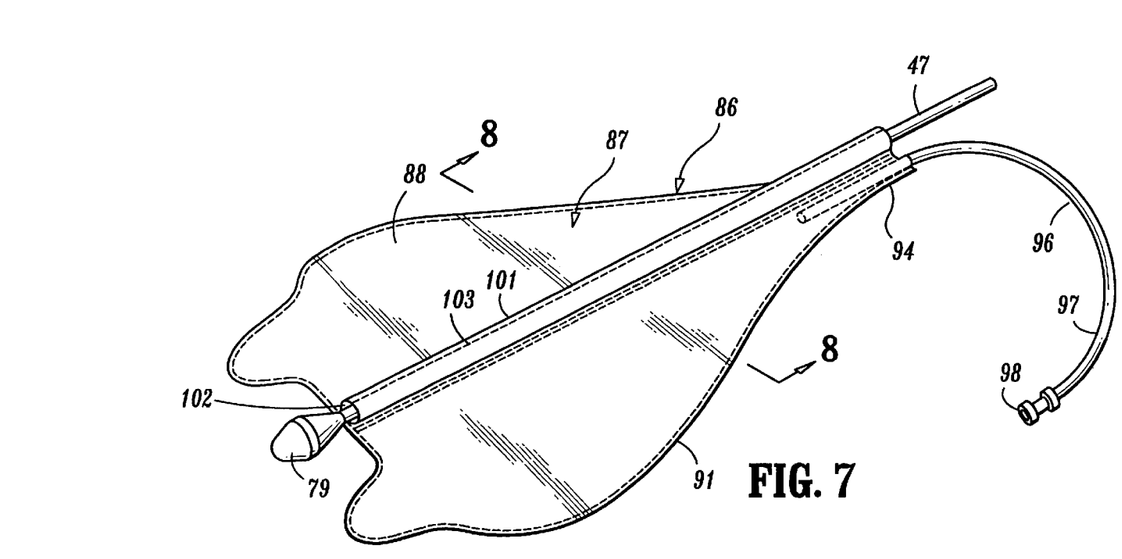
FIG. 7 is a perspective view of a balloon shaped according to the present invention together with inflation and tunneling means associated therewith.
Figure 8:
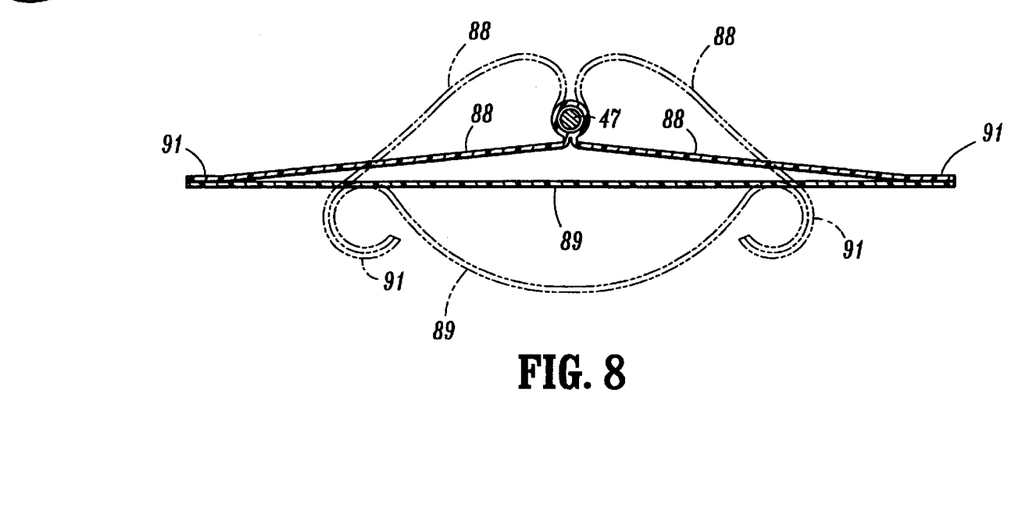
FIG. 8 is a cross-sectional view of the balloon of FIG. 7.

Alternatively, as shown in FIG. 5, a balloon 1, preferably formed from a non-elastic material such as polyurethane or polyvinyl chloride, is provided with protuberances 2 extending from the distal region of the balloon. Before inflation, the protuberances 2 are everted within the balloon 1 as shown by the dashed lines indicated by the reference numeral 3. This permits the balloon 1 to be rolled or folded into a compact arrangement, e.g., around a substantially rigid tunneling member has shown in FIG. 7. As shown in FIGS. 5 and 6, the balloon may have a central protuberance 5 or, as shown in FIGS. 7 and 8, the balloon may have no central protuberance. Furthermore, the central protuberance 5 may be longer in axial dimension than shown in FIG. 5. In some embodiments, the central protuberance serves the purpose of facilitating the proper placement of a substantially rigid tunneling shaft in the balloon with the distal end of the tunneling shaft residing in the central protuberance, e.g., by passing the tunneling shaft through passage 6 in the balloon.

As shown in FIG. 6, once inflated, the balloon 1 has dissected the space of Retzius, but protuberances 2 have avoided dissection in a manner which would risk damage to the pubic symphysis 9 or the medial neurovascular bundle 8. The pubic bones are indicated by the numeral 7 and are connected by the pubic symphysis 8.

Balloons having the general shape shown in FIGS. 5–8 have been found to be particularly efficacious for use in bladder-neck suspension procedures. Such procedures generally seek to elevate the urethrovesical junction (bladder neck) in order to restore more normal anatomy as therapy genuine urinary stress incontinence. The suspension is often accomplished with sutures in the periurethral tissue to lift the bladder neck, but avoid damage to medial vasculature. Bladder-neck suspension procedures are now well known and are performed to correct female incontinence problems, particularly genuine stress incontinence. There are several recognized bladder-neck suspension procedures. One is the "Burch" procedure described by J. C. Burch in Am.J.Obstet.Gynecol. 1968; 100:764–774 which was introduced in about 1955. Still earlier, Drs. Marshall, Marchetti and Krantz developed a bladder-neck suspension procedure which is disclosed in their article in Surg.Gyn.Obstet. 1949; 88:509 and which has, because of the initials of these three doctors, become known as the "MMK" procedure. The disclosures of the aforesaid Burch and Marshall, Marchetti and Krantz articles are incorporated herein by reference in their entireties. These bladder-neck suspension procedures elevate the urethra vesicular junction ("UVJ" or "bladder-neck") in order to correct sagging of the bladder-neck. When such sagging occurs, there is a reduction in the pressure retention capability of the urethra and related anatomy during moments of stress such as coughing, physical exertion and the like. This suspension is accomplished with sutures on either side of the urethra which, in the MMK procedure pass through the periosteum of the pubic bone and, in a Burch procedure, through the periurethral tissue and Cooper's ligament. More recently, the MMK procedure has been modified to use bone anchors in the pubic bone rather than the periostium as the site of one end of the suture connection. Such procedures are described in U.S. Pat. Nos. 5,217,486; 5,207,679 and 4,899,743, the disclosures of which are incorporated herein by reference. Such procedures are also described in my patent application Ser. No. 08/664, 051, filed Jun. 13, 1996, the disclosure of which is incorporated by reference herein.

The minimally invasive versions of these procedures require dissection of the space of Retzius, which is a retropubic space and an inferior extension of the preperitoneal space between the pubic symphysis and the bladder. Balloon dissection is a useful technique in this regard. Whenever balloon dissection is carried out in the preperitoneal space, it is advantageous if Cooper's ligament is at least partially denuded by expansion of the balloon itself. Before Cooper's ligament is exposed, there are few landmarks to orient the surgeon and he must proceed with careful manual dissection as he creates his working space. In contrast, if Cooper's ligament is exposed by the balloon, its white appearance provides an immediate landmark for the surgeon, his orientation is immediate, and tedious manual dissection is reduced or eliminated.

In the inferior anatomy, there are important structures which must be respected during dissection. In addition to the bladder itself, there are important vascular and nerve complexes both medial and lateral, at the level of and inferior to the pubis. It is therefore important that the balloon means, although inherently gentle, minimize trauma to these structures, but still accomplish sufficient safe dissection to afford visualization if needed, provide access to Cooper's ligament between the medial and lateral vessels for suture attachment, and promote scarring and hence adhesions to reinforce the suture suspension post-operatively.

This invention provides for two inflatable extensions distal of the main body of the balloon which may optionally be inverted, folded, or rolled independently of the main body of the balloon. If inverted, the cross-sectional aspect of the extensions may be sized to assure sequential inflation after the main body of the balloon is inflated. In this manner, the main body can be made to act as an anchor from which the extensions may extend in a controlled manner. If spaced appropriately, the extensions will dissect a safe area between delicate medial and lateral structures quite effectively. Independently, the main body of the balloon may be shaped to suit the surgeon preference or procedure.

The balloon 1 may have an elongate neck such as that indicated by reference numeral 4 and may be utilized with any of the various embodiments of tunneling apparatus disclosed in application Ser. No. 08/570,766, filed Dec. 12, 1995, which is incorporated herein by reference.

FIG. 7 illustrates a balloon 87 configured according to the present invention. Balloon 87 is preferably formed of a non-elastomeric, medical grade material of a suitable type such as polyvinyl chloride or polyurethane. Balloon 87 can be formed of two sheets, 88 and 89, of such material which have their outer margins bonded together by suitable means such as by heat at margin 91 extending around the parameter of balloon 87. Alternatively, balloon 87 may be a single molded piece.

Balloon 87 is also provided with neck 94 into which flexible tubular member 96 extends. Tubular member 96 is secured to balloon 87 in a suitable airtight fashion, such as by an adhesive. The tubular member 96 is provided with a lumen 97 which is in communication with the interior of the balloon 87 and which can be used for inflating balloon 87 through a Luer-type fitting 98 mounted on the tube 96.

Means are provided for removably securing balloon 87 to tunneling shaft 47, such as by sleeve 101 formed of the same material as balloon 87, and which can be formed integral or separate therefrom and adhered thereto by suitable means such as an adhesive. The sleeve 101 extends longitudinally of the balloon 87 and is typically, but not necessarily, disposed generally equidistant from the side margins thereof. The sleeve 101 is provided with passage 102 extending therethrough which is sized to slidably accommodate the tunneling shaft 47. Means are provided for permitting separation of balloon 87 from the tunneling shaft 47 and may take the form of longitudinally spaced apart perforations 103 in sleeve 101 extending along sleeve 101. Perforations 103 are spaced closely enough together to form a weakened region so that the balloon can readily be separated from the tunneling shaft 47 by tearing along perforations 103 in sleeve 101. The distal portion of sleeve 101 can be provided with means, e.g., a radially extending ridge, which will create a tighter fit with shaft 47 and inhibit axial movement of balloon 87 when a removable sleeve (not shown) is withdrawn.

As shown in FIG. 8, which is a cross-sectional view taken along line 8—8 of FIG. 7, when balloon 87 is deflated, its side margins can be rolled inwardly toward tunneling shaft 47 as shown by the broken lines in FIG. 8. When in its rolled-up configuration, balloon 87 can be enclosed within a removable sleeve (not shown) which comprises a cylindrical tube as shown, e.g., in application Ser. No. 08/717,794, filed Sep. 20, 1996, which is incorporated herein by reference.

Figure 9:
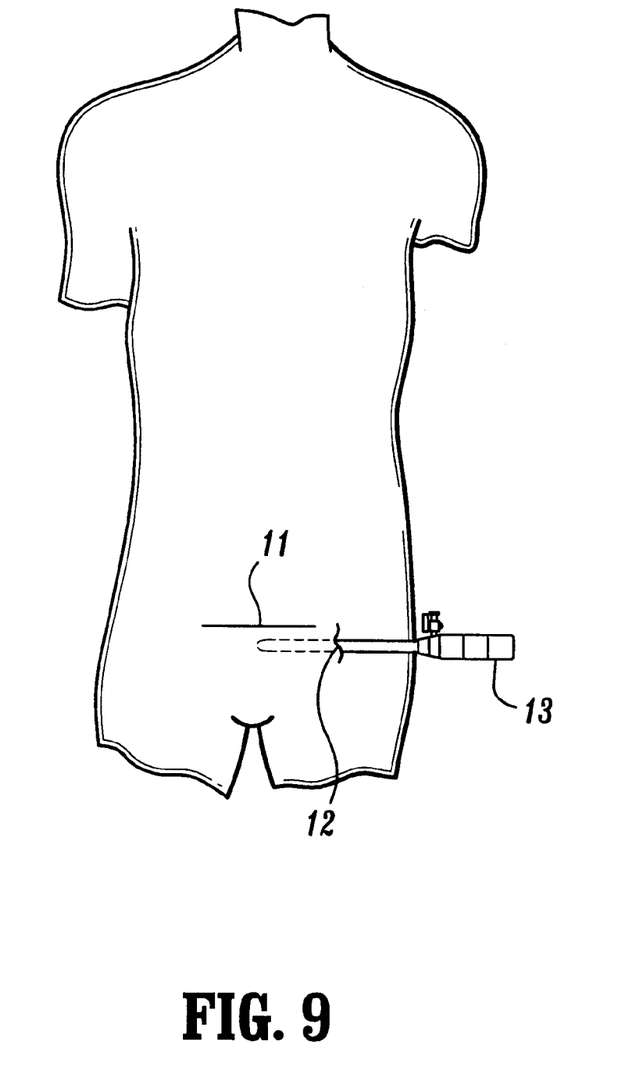
FIGS. 9 and 10 illustrate still another embodiment of the present invention.

In the embodiments described above, insertion of the dissecting device towards the space of Retzius generally proceeds inferiorly from near the umbilicus. However, it is not unusual that a female, by the time she presents with genuine stress incontinence, has experienced previous abdominal procedures, caesarean childbirth, or other abdominal trauma to make an umbilical approach difficult, if not impossible because of scarring. At the very least, penetration through the peritoneum is likely. In cases of scarring, as shown in FIG. 9, a Pfannenstiel scar incision (11) is perhaps the most inferior type of scar likely to be encountered. These are transverse about the midline, and generally 3 to 5 cm above the pubis. They impede the tunneling of a balloon dissector from the umbilicus.

With some bladder neck procedures it may not be necessary to develop working space above the Pfannenstiel scar in order to carry out the procedure. A balloon dissector 13 can be inserted through a lateral cut down 12 just inferior to the Pfannenstiel scar, and can be tunneled laterally just below the scar to the other side, taking care to stay anterior to the peritoneum. The balloon can then be inflated. If shaped to open esentially to the inferior side only, a space from the Pfannenstiel scar downwards can be developed.

After dissection, the urethropexy can proceed. In many instances, this inferior space may be more convenient than one developed from a more superior incision.

Figure 10:
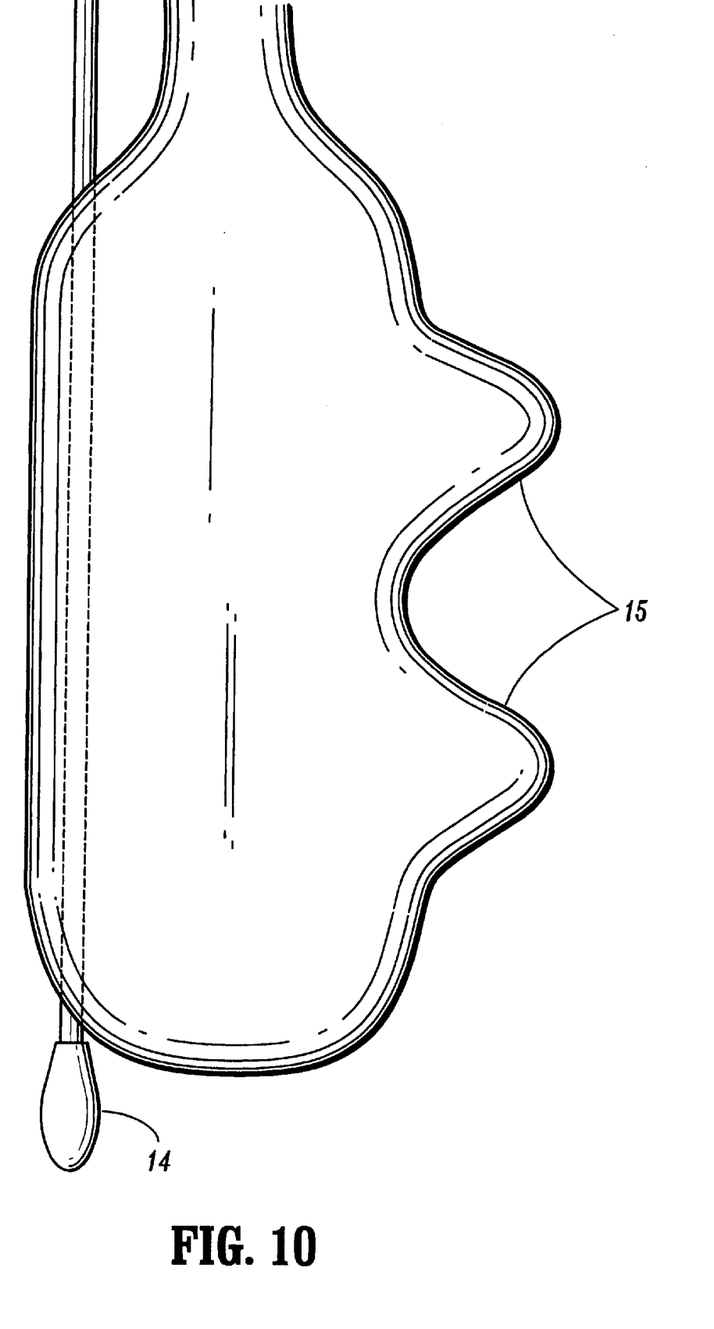
Figures 11A, 11B, 11C:
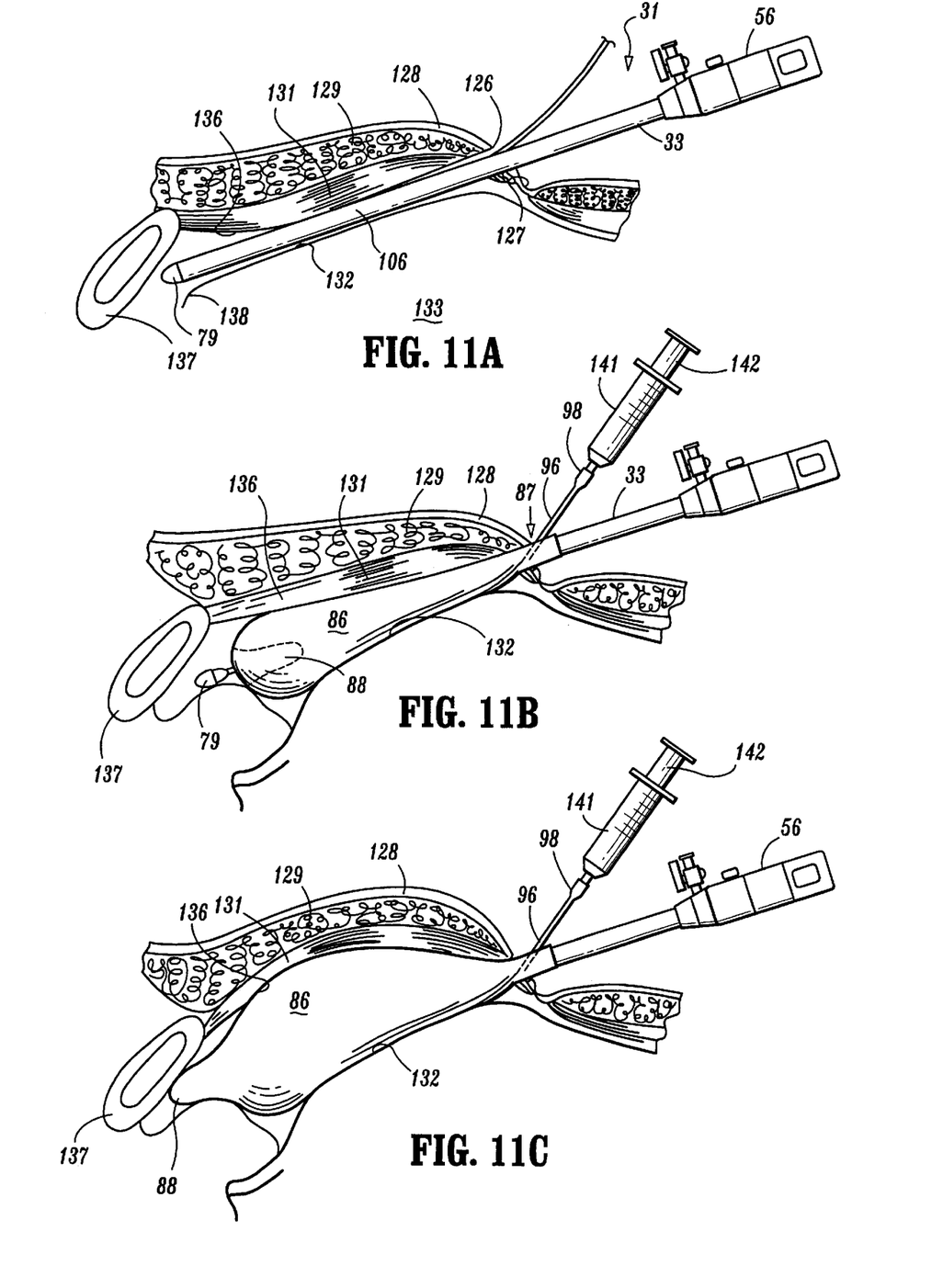
FIGS. 11A–11C illustrate the sequence of use of the device of this invention.

A suitable balloon for the purpose of dissection inferior to a Pfannenstiel scar is as shown in FIG. 10. It is asymmetrical about the tunneling number 14, and has horns 15. As described above, these may be inverted for sequential deployment, or they may merely be rolled or gathered adjacent to the tunneling member. A balloon cover, as previously described and referenced will facilitate tunneling of the device, and positioning such that the larger side will deploy inferiorly. On inflation, the dissected space below the scar will be similar to the inferior portion of the device described above which is tunneled from the umbilicus The sequence of balloon introduction on a tunneling shaft 79, inflation of the balloon 87 and inflation of the protuberances 88 is shown in FIGS. 11A, 11B and 11C. The patient is prepared in an appropriate manner by administering a suitable anesthesia, as for example a spinal anesthesia, and any other necessary preparation. The surgeon first makes an inframbilical incision 126 in the skin below the navel or umbilicus 127 and separates the fat 129 and then incises the anterior rectus sheath or fascia 131 in the midline. Care should be taken not to penetrate the peritoneum 132 overlying the abdominal cavity 133 (see FIG. 11A).

After the incision 126 has been made in the manner hereinbefore described, the laparoscopic apparatus 31 is then taken by one hand of the surgeon, grasping the handle 56 and utilizing the other hand to facilitate the insertion of the rounded blunt tip 79 into the incision 126. The blunt tip 79 is caused to enter the slit in the fascia 131 and pass anterior to the peritoneum 132, in between the rectus muscles (laterally), and enters the potential preperitoneal space 136. The blunt tip 79 is then utilized as a tunneling device by the surgeon using one hand 56 to advance the blunt end 79 toward the pubic region of the patient while the surgeon places his other hand on the abdomen to feel the apparatus or device 31 as it is being advanced. The advance of the device 31 is continued until the blunt tip 79 is below the symphysis pubis 137 as shown in FIG. 11B, and preferably is disposed between the symphysis pubis 137 and the bladder 138.

After the apparatus or device 31 has been properly positioned as shown in FIG. 11B, the removable sleeve or sheath 106 is removed by the surgeon using one hand to engage the proximal portion of device 31 which is exterior of the body of the patient and outside of the incision 126. At the same time, the other hand of the surgeon is utilized to stabilize the portion of the device 31 which is within the preperitoneal space. The sheath 106 can be readily withdrawn since it is formed of Teflon and is split or weakened along its length, by pulling it proximally and away from the longitudinal axis of the tubular member 33. As the sheath 106 opens and slips off, it exposes the balloon 87 of the balloon assembly 86. When the sheath 106 is completely removed, a sterile saline solution serving as a balloon inflation medium is introduced into the balloon 87 through the tubular member 96 by connecting a conventional syringe 141 to the Luer fitting 98. The balloon 87 typically can be inflated to a suitable size by introducing 500 cc or less of normal saline solution into the balloon 87 by pressing on the plunger 142. As the balloon 87 is inflated, the balloon 87 progressively unwraps with its side margins rolling outwardly from the center while expanding into a plane to cause progressive separation or dissection of tissue (i.e. 131, 132) along its weakest points by application of forces generally perpendicular to the plane of the balloon 87 as to create the peritoneal or anatomic space.

As shown in FIG. 11C, further inflation of the balloon causes protuberances 88 to inflate around the pubic symphysis without disrupting it.

After the desire bloodless anatomic space or pocket 136 is formed, the balloon 87 is deflated by withdrawing the normal saline solution by withdrawal of plunger 142 of the syringe 141 or via a hospital vacuum aspirator. After the balloon 87 has been deflated, the balloon assembly 86 can be removed by grasping the handle 56 of the laparoscopic apparatus or device 31 with one hand and using the other hand to grasp the tubular member 96 and the proximal extremity of the balloon 87 and to remove the same through the incision 126. Bladder neck suspension can then be performed as described above.

A suitable material for fabrication of the balloon of the present invention is 0.004 inch thick polyurethane film such as PS-8010 supplied by Deerfield Urethane, Inc. of South Deerfield, Mass.

From the foregoing, it can be seen that the apparatus and methods of the present invention can be utilized in connection with various laproscopic surgical procedures and in particular with bladder neck suspension procedures. While embodiments and applications of the disclosed devices and associated methods have been shown and described, it will be apparent to those skilled in the art that the foregoing specific embodiments can be modified without departing from the scope of the present invention. Thus, the present invention is of the full scope of the claims appended hereto.

I claim:

1. A balloon device for use in laparoscopic surgery comprising a balloon having a main body and having at least two inflatable inverted protuberances in its distal end, wherein said at least two inflatable inverted protuberances evert outwardly sequentially after said main body inflates.

2. The device of claim 1 wherein said balloon, when deflated, is generally pear-shaped.

3. A balloon device for use in laparoscopic surgery comprising a balloon having a main body and having at least two inflatable inverted protuberances in its distal end, wherein said at least two inflatable inverted protuberances evert outwardly sequentially after said main body inflates, wherein said balloon is mounted on a tunneling shaft.

4. The device of claim 3 wherein said balloon, when deflated, is rolled-up and adjacent to said tunneling shaft.

* * * * *